United States Patent [19]

Inkson et al.

[11] 4,316,012
[45] Feb. 16, 1982

[54] RECOVERY OF XANTHAN GUM

[75] Inventors: Michael B. Inkson; Clive K. Wilkinson, both of Reading, England

[73] Assignee: Talres Development (N.A.) N.V., Netherlands Antilles

[21] Appl. No.: 182,504

[22] Filed: Aug. 29, 1980

[30] Foreign Application Priority Data

Oct. 29, 1979 [GB] United Kingdom ............... 37364/79

[51] Int. Cl.$^3$ ...................... C08B 37/00; C12D 13/00
[52] U.S. Cl. ...................................... 536/114; 435/104
[58] Field of Search ..................... 536/114, 1; 435/104

[56] References Cited

U.S. PATENT DOCUMENTS

| 3,232,929 | 2/1966 | McNeely | 536/114 |
| 3,355,447 | 11/1967 | O'Connell | 536/1 |
| 3,591,578 | 7/1971 | Colin et al. | 536/114 |
| 4,135,979 | 1/1979 | Corley et al. | 536/114 |

Primary Examiner—Blondel Hazel
Attorney, Agent, or Firm—Ostrolenk, Faber, Gerb & Soffen

[57] ABSTRACT

Xanthan gum is recovered from an aqueous fermented broth containing the gum by adding to the broth a subprecipitant amount of organic solvent such an isopropanol, removing solids from the broth at 100° C. or more, eg. by filtration, and precipitating the gum by addition of more organic solvent. Heat degradation of the gum during the solids removal is thereby lessened.

9 Claims, No Drawings

RECOVERY OF XANTHAN GUM

The present invention relates to the recovery of xanthan gum.

Xanthan gum is an exocellular polysaccharide produced during fermentation of carbohydrates by *Xanthomonas campestris* and other bacteria of the genus Xanthomonas. The gum is manufactured on an industrial scale, and is used for example as a thickener in foods and as a viscosity control agent during secondary recovery of oil.

Fermentation of a xanthan-producing micro-organism on a continuous or batch basis gives a viscous broth or beer which in addition to the desired gum contains other matter, eg non-assimilated nutrients, cells of the micro-organism or cell debris. Various techniques are available for purifying the xanthan gum such as the sequence comprising precipitation of the gum by addition of isopropanol or the like precipitating agent, filtration, removal of excess precipitating agent from the recovered solid, and comminution of the resultant solid material. This sequence gives a solid product which also contains the solids (for instance cells of the xanthan-producing bacterium) which were present in the fermented broth.

In U.S. Pat. No. 3,355,447, it is disclosed that the properties of the ultimate product, especially the clarity and stability can be improved by heating the fermented broth at a pH of 7 to 9 to a temperature of from 150° F. (about 66° C.) to 170° F. (about 77° C.). The broth is held at this elevated temperature for at least 20 minutes and is then cooled to from 40° F. (about 4° C.) to 100° F. (about 38° C.). The concentration of colloidal gum is adjusted to be 1% by weight or less, usually by adding cold water as part of the cooling to from 40° to 100° F., and the cooled gum is then filtered. Thereafter the gum can be recovered from the filtrate by the purification sequence given above.

In U.S. Pat. No. 3,591,578, it is explained that it is possible to use higher temperatures for the heat treatment than are disclosed in the U.S. Pat. No. 3,355,447. More specifically, U.S. Pat. No. 3,591,578 proposes heating the fermentation broth to from 80° to 130° C. for 10 to 20 minutes.

UK Patent No. 1488645 acknowledges that heat treatment is a conventional post-fermentation procedure, mentioning the use of pasteurization for 1 to less than 3 minutes at 91° to 96° C. and referring also to the suggestion of heating from 80° to 130° C. for 10 to 120 minutes. In its turn, the UK Patent No. 1,488,645 espouses a heat treatment of from 120° F. (about 99° C.) to 220° F. (about 104° C.) for from 1 to 5 minutes. The limit of 5 minutes is said to be critical, with prolonged heat-exposure resulting in a decreased viscosity.

It now seems to be generally accepted in the art that some form of heat treatment of the fermented broth can be beneficial especially in improving the viscosity of the product. Thus, as a recent example, UK Patent Application No. 2,012,792 adopts a heat treatment of from 1 to 40 minutes at from 80° to 130° C.

UK Patent No. 1,528,316 suggests a hot filtration process in which a fermentation broth containing at least 1% by weight xanthan gum is filtered at a temperature of at least 112° C. The hot filtration is a faster procedure than filtration at the more conventional, lower temperatures and as such the process is effective with broths containing around 2% by weight gum. It will be recalled that in the process of the U.S. Pat. No. 3,355,447 there is the requirement that the gum concentration is adjusted to be 1% or less before the filtration is attempted.

We have been evaluating on a laboratory scale the procedures which are available for the purification of xanthan gum, and in particular have been considering how to improve upon them. The utility of a heat treatment does not seem in doubt, but even with a hot filtration, we find it difficult to achieve fast filtration rates: the hot filtration technique has the disadvantage that thermal degradation of the gum occurs if it is exposed to too much heat during a slow separation.

According to the present invention, we provide a process for the recovery of xanthan gum from an aqueous fermented broth containing the gum, in which process a sub-precipitant amount of organic solvent is added to the broth, solids are removed from the diluted broth at a temperature of at least 100° C., and the gum is then precipitated by addition of organic solvent to the resultant liquid resulting after the solids removal.

In our process, we employ as a diluent in a hot separation for solids removal, an organic solvent which is a precipitating agent for precipitation of xanthan gum.

During the conventional recovery of xanthan gum, it is a standard procedure to precipitate out the gum using a precipitating agent such as isobutanol or isopropanol. Other organic solvents can be used as precipitating agents, eg methanol, ethanol, t-butanol, acetone etc.

However, in the present process the organic solvent is added to the broth itself in a sub-precipitant amount, ie. an amount which is less than that required to precipitate out the gum.

No appreciable precipitation of the gum occurs as a result of adding the organic solvent to the fermented broth, and unwanted solids can be removed from the diluted broth eg. by filtration or by centrifugation. Only after removal of solids is sufficient organic solvent added to effect precipitation of the gum. The total volume of solvent employed in the present process need not necessarily be greater than the volume required for precipitation of the gum directly from the broth.

The preferred organic solvent for the present process is isopropanol, ie. propan-2-ol, often referred to as IPA. A sub-precipitant amount of IPA is typically less than one volume of IPA for each volume fermented broth. Particularly with broths of low gum concentration, it may be possible to add a volumetric excess of IPA without causing appreciable gum precipitation. On the other hand, little extra advantage is obtained by working our process at the limit where the volume of diluent added to the broth before solids removal is only just less than that which brings about appreciable gum precipitation.

Thus, the ratio of IPA volume to broth volume when adding IPA before solids removal is preferably from 0.25:1 to 0.95:1, more preferably from 0.6:1 to 0.9:1, and most preferably around 0.8:1. These ratios are quoted on the basis that the IPA is 100% IPA; if desired, an industrial grade of aqueous IPA can be used. For example, the most preferred IPA: broth volumetric ratio of 0.8:1 can be attained by mixing equal volumes of 80% IPA and broth.

The diluent organic solvent need not be IPA. Other precipitating agents are known, and examples are given above. These agents can now be employed in sub-precipitant amounts for the present purposes, with the solvent: broth ratio typically being 0.9:1 or less, eg. 0.6:1 to 0.9:1. Greater volumes of solvent can be added before solids removal, provided that the addition does not bring about appreciable precipitation.

After addition of the solvent to the broth, the diluted broth is filtered, centrifuged, or otherwise processed, at a temperature of at least 100° C. to remove solids. The preferred temperature is in the range 100° to 115° C., with 105° to 110° C. being especially suitable, but higher temperatures can be used. In practice, there is an upper limit to the temperature determined by the thermal stability of the gum being filtered. For this reason, we regard 130° C. as the maximum temperature for the solids removal.

Solids removal is preferably effected by filtration. The filtration equipment can be conventional, with a pressure leaf filter being particularly appropriate. Filter aid can be coated on such a filter before filtration is begun, and filter aid can also be added to the diluted broth being filtered.

By virtue of the addition of the solvent, the hot broth can be separated from the solids at a faster rate than would otherwise be obtained at the operating temperature. Conversely, a given separation rate can be obtained at a lower temperature.

Xanthan gum is then recovered from the resultant liquid by addition of more organic solvent. For most purposes, it is convenient if the solvent added to the liquid is the same as that added as diluent before solids removal. In this way, it is easier to calculate the appropriate volumes of solvent and it is also easier to recover the solvent after the gum recovery.

The volume of solvent added to the resultant liquid is sufficient to precipitate the gum, and typically will be such as to bring the volume of solvent in the liquid up to at least 1.1 times the volume of water in the liquid. Less solvent may sometimes be appropriate, but we prefer that the volumetric ratio of solvent to water in the liquid is from 1.3:1 to 3:1, more preferably 1.3:1 to 2:1.

The precipitated gum can then be separated in a conventional manner, eg by decantation, and further treated as desired, eg to remove excess solvent from the gum and/or to improve the granularity of the gum. Techniques for these and other treatments are known per se and further details are unnecessary.

We find that by adoption of our process it is possible to obtain a relatively fast solids removal, typically 50 or 100% faster than would be obtained without addition of the solvent to the fermented broth. Moreover, the faster separation is achieved without giving rise to unacceptable thermal degradation of the product. Indeed, we find that both the viscosity and the purity of the product are improved by use of a hot filtration with dilution.

The present invention is illustrated by the following non-limiting examples:

EXAMPLE 1

Xanthan solution was admixed with 80% propan-2-ol in the ratio 1:1 w/v and filtered at 110° C. through a $1.6 \times 10^{-3} m^3$ pressure leaf filter. Filter aid concentration was 0.5% Celite 545 and a precoat of $0.25 Kg.m^{-2}$ of cellulose extrainer was first laid down.

An average filtration rate of $9.2 \times 10^{-7} m^3 s^{-1}$ was achieved. An increase in broth viscosity from a 0.1% K value of 0.65 to 0.88 $Nm^{-2}s$ occurred and the purity was improved (% decarboxylation increased from 4.34 to 4.53%). The pyruvate concentration remained essentially constant at 2.6%.

Comparative Example 1

The same xanthan gum solution as used in Example 1 was filtered at 110° C. without first admixing the solution with propan-2-ol. An average filtration rate of $1.7 \times 10^{-8} m^3 s^{-1}$ was achieved. No increase in broth viscosity from a 0.1% K value of $0.65 Nm^{-2}s$ occurred and decarboxylation increased from 4.34 to 4.4%. Pyruvate concentration decreased from 2.7 to 0.6%.

EXAMPLE 2

A xanthan gum solution admixed with 80% propan-2-ol in the ratio 1:1 w/v was filtered at 105° C. as in example 1. An average filtration rate of $8.15 \times 10^{-7} m^3 s^{-1}$ was achieved. An increase in broth viscosity from a 0.1% K value of 0.50 to 0.73 $Nm^{-2}s$ occurred. The purity was improved (% decarboxylation increased from 3.40 to 3.85%) and pyruvate concentration increased from 5.5 to 5.9%.

We claim:
1. A process for recovery of xanthan gum from an aqueous fermented broth containing xanthan gum and solids, which process consists essentially of adding isopropanol (IPA) to said broth to give a diluted broth, said IPA being added in a sub-precipitant amount of an IPA:broth volume ratio of 0.6:1 to 0.95:1; removing solids from said diluted broth at a temperature of at least 100° C. and thereby giving a resultant liquid; and then precipitating said gum by addition of IPA to said resultant liquid.

2. The process of claim 1, wherein the IPA:broth volume ratio is about 0.8:1.

3. The process of claim 1, wherein said diluted broth is at a temperature between 100° and 115° C. for the step of removing solids.

4. The process of claim 1, wherein said solids are removed from said diluted broth by filtration.

5. The process of claim 1, wherein the volume of said IPA added to said resulting liquid brings the volume of IPA in said resulting liquid to at least 1.1 times the volume of water in said liquid.

6. The process of claim 1 wherein said diluted broth is at a temperature of 105° to 110° C. for the step of removing solids.

7. The process of claim 1, wherein the volume of said IPA added to said resulting liquid brings the volume of IPA in said resulting liquid to 1.3–3 times the volume of water in said liquid.

8. The process of claim 7, wherein the volume of said IPA added to said resulting liquid brings the volume of IPA in said resulting liquid to 1.3–2 times the volume of water in said liquid.

9. The process of claim 8, wherein the IPA:broth volume ratio is about 0.8:1, said diluted broth is at a temperature of 105°–110° C. for the step of removing solids and said solids are removed from said diluted broth by filtration.

* * * * *